United States Patent [19]

Sustmann et al.

[11] Patent Number: 4,675,014

[45] Date of Patent: Jun. 23, 1987

[54] MICROBISTATIC AND DEODORIZING CATAMENIAL AND HYGIENIC DEVICES

[75] Inventors: Scarlet Sustmann, Viersen, Fed. Rep. of Germany; Ingo G. Marini, Lenzing, Austria

[73] Assignee: Henkel Kommanditgesellschaft auf Aktien, Duesseldorf, Fed. Rep. of Germany

[21] Appl. No.: 707,706

[22] Filed: Mar. 4, 1985

[30] Foreign Application Priority Data

Mar. 6, 1984 [DE] Fed. Rep. of Germany ....... 3408130

[51] Int. Cl.$^4$ ............................................. A61F 13/16
[52] U.S. Cl. .................................... 604/375; 604/360
[58] Field of Search ............... 604/375, 376, 360, 359; 424/26–28

[56] References Cited

U.S. PATENT DOCUMENTS

| | | | |
|---|---|---|---|
| 2,856,330 | 10/1958 | Vagenius | 167/84 |
| 3,059,013 | 10/1962 | Musser | 424/28 |
| 3,067,745 | 12/1962 | Burgeni | 424/28 |
| 3,536,437 | 10/1970 | Rogovin et al. | 8/17 |
| 3,542,504 | 11/1970 | Schofield et al. | 8/116.2 |
| 3,658,790 | 4/1972 | Bernardin | 604/375 |
| 3,794,034 | 2/1974 | Jones, Sr. | 604/360 |
| 3,971,379 | 6/1976 | Chatterjee | 604/376 |
| 4,296,234 | 10/1981 | Mindt et al. | 604/375 |
| 4,385,632 | 5/1983 | Odelhög | 604/375 |
| 4,454,055 | 6/1984 | Richman | 604/376 |

FOREIGN PATENT DOCUMENTS

| | | | |
|---|---|---|---|
| 0019371 | 12/1985 | European Pat. Off. | 604/360 |
| 3135410 | 6/1982 | Fed. Rep. of Germany . | |
| 1499358 | 9/1966 | France . | |
| 2083748 | 7/1981 | United Kingdom . | |

*Primary Examiner*—John D. Yasko
*Attorney, Agent, or Firm*—Ernest G. Szoke; Henry E. Millson, Jr.; Mark A. Greenfield

[57] ABSTRACT

A method for absorbing bodily secretions while hindering the generation of odors and growth of microbes comprising applying a fibrous mass having copper cations bound through selected anions, preferably carboxymethyl, the amount of chemically bound copper being between 0.1 and 3% by weight. The fibrous mass can be in the form of a catamenial device, bandage, diaper, shoe liner, or the like.

31 Claims, No Drawings

MICROBISTATIC AND DEODORIZING CATAMENIAL AND HYGIENIC DEVICES

BACKGROUND OF THE INVENTION

1. Field of the Invention

This invention relates to hygienic devices and catamenial devices such as tampons, sanitary napkins, panty shields, panty liners, and the like, comprised of a novel microbiostatic and deodorizing fibrous material.

2. Statement of the Related Art

It is known that, in sanitary hygienic and catamenial devices which consist of an absorbent fibrous material and which are used for absorbing bodily secretions, such as blood, urine, menstrual fluid, lymphatic fluids and perspiration, bacterial decomposition of the secretion begins after only a short time under the effect of ubiquitously present bacteria and is accompanied by the emission of an unpleasant odor. In addition, serious health risks are presented by the growth of pathogenic, particularly alkaliphilic, microbes. There has been no shortage of attempts to provide sanitary hygiene aids of absorbent fibrous materials with deodorizing and microbistatic properties. Various microbicides and deodorants suitable for suppressing body odor have been proposed for this purpose.

However, suppressing the odor generated by the decomposition of blood, urine, menstrual fluid, lymphatic fluid, perspiration, and the like, is a comparatively difficult problem, particularly because the usual antimicrobial agents are not firmly anchored to the fibers and are readily leached by the above-mentioned secretions. It has also been proposed to use copper compounds for treating fibrous materials for sanitary hygiene aids.

U.S. Pat. No. 4,385,632 (and corresponding German published application 31 35 410) describe an absorbent padding of nonwoven cellulose fibers or wadding which is sprayed with an aqueous solution of a copper salt or prepared from fibers or wadding pre-treated with such a solution. Disclosed suitable copper salts are the borate, sulfate, chloride, formate, oxolate, tartrate, citrate, lactate, and especially, the acetate. This known material is attended by various disadvantages. Thus, the copper salt is not uniformly distributed in the absorbent padding, some of the copper salt crystallizes out after drying (which gives rise to difficulties during processing of the fibrous material), and the copper salt dissolves in the presence of water, for example, in a wet diaper or in a damp tampon, and can thus reach the surface of the skin in relatively high concentrations, producing undesirable reactions.

Published European Patent Application No. 19,371 describes a blood-coagulating absorbent material consisting of a water-swellable, covalently crosslinked anionic polyelectrolyte, for example crosslinked carboxymethyl cellulose, which is treated with transition metal ions, such as with copper ions. Disclosed salts for treatment include copper chlorides, nitrates, sulfates and acetates in one process and copper carbonates, oxides or hydroxides in a second process. However, materials such as these are not themselves usually fibrous or cannot readily be converted into fibers, wadding or nonwovens. It is disclosed that the materials may be processed with a fibrous carrier as a support when used in hygiene aids. Both the manufacture and also the processing of this material are difficult.

DESCRIPTION OF THE INVENTION

The present invention provides sanitary hygiene aids employing an absorbent fibrous material which has permanent deodorizing and microbistatic properties, i.e. which cannot be washed out, and which is easy to make and process. Other than in the operating examples, or where otherwise indicated, all numbers expressing quantities of ingredients or reaction conditions used herein are to be understood as modified in all instances by the term "about".

This is achieved by producing sanitary hygiene aids which comprise completely or partly an absorbent fibrous material which consists essentially of cellulose fibers modified by anionic salt-forming moieties and contains copper chemically attached to the fibers through those anionic moieties. In the context of the invention, cellulose fibers are understood to be cellulose, cotton and/or viscose fibers.

Anionic salt-forming moieties may be incorporated in the cellulose molecule in various ways. Anionically modified cellulose fibers such as these are known and, in some cases, are also commercially available. Suitable cellulose fibers of the type in question are, for example, cellulose fibers which carry at least one of the moieties of the general formulae: $-PO_3H^{(-)}$; $-(CH_2)_n-PO_3H^{(-)}$; $-(CH_2)_n-SO_3^{(-)}$; or $(CH_2)_n-COO^{(-)}$; (where n may have a value of from 1 to 3); which are attached via the oxygen to the anhydroglucose units. Known cellulose derivatives of this type include: cellulose phosphate obtainable by esterifying cellulose with phosphoric acid: phosphonoethyl cellulose obtainable by etherifying alkali cellulose with chloroethyl phosphonate: phosphonomethyl cellulose obtainable by etherifying cellulose with chloromethyl phosphonate: sulfoethyl cellulose obtainable by etherifying cellulose with chloroethane sulfonate and the similarly obtainable sulfomethyl cellulose and sulfopropyl cellulose. Also useful is 1-sulfo-2-hydroxypropyl cellulose which may be obtained by cellulose etherification with 1-chloro-2-hydroxypropane sulfonate.

Carboxyl groups may be introduced into the cellulose molecule in two basically different ways: by the physical incorporation of carboxyl-containing compounds in the viscose, i.e. in a cellulose dissolved in the form of cellulose xanthogenate, to form incorporated viscose fibers (alloy fibers) or by the chemical reaction (etherification) of the fiber-forming cellulose with carboxyl-containing reagents to form cellulose fibers uniformly modified by, for example, carboxyalkyl groups corresponding to the formula $-(CH_2)n-COOH$, in which n may have a value of from 1 to 3.

The physical incorporation of compounds containing carboxyl groups in the viscose is obtained, for example, by the addition of alkali salts of acrylic acid homopolymers, acrylic acid-methacrylic acid copolymers, methyl vinyl ether-maleic acid anhydride copolymers, alginic acid or carboxymethyl cellulose to the viscose solution, followed by spinning in the usual way into a precipitation bath. Commercially available fibers of the type include fibers which are a blend of viscose and acrylic acid-methylacrylic acid copolymer, sold by Enka under the trademark ABSORBIT. Fibers such as these are not uniformly modified, but instead are made up of modified and unsubstituted fiber fragments.

Cellulose fibers chemically modified throughout by carboxyalkyl groups are particularly preferred for producing the fibrous materials of this invention. In fibers such as these, the entire fiber-forming cellulose is uniformly modified. They may be obtained by carboxymethylating cellulose fibers with sodium chloroacetate, immediately after conversion into alkali cellulose. The cellulose thus modified may be improved in its fiber structure by the viscose spinning process. However, a viscose fiber regenerated by the viscose spinning process may also be subsequently carboxymethylated with chloroacetic acid. A third possibility of obtaining cellulose fibers uniformly modified with carboxyalkyl groups is to add sodium chloroacetate to the viscose solution during xanthogenation and then spin the carboxymethylated viscose in the usual way. Viscose fibers such as these, uniformly modified by carboxymethyl groups, are commercially available from Lenzing AG under the trademark VISCOSORB lN.

If acrylonitrile is added to the viscose solution during xanthogenation, viscose fibers consisting of carboxyethyl cellulose having a low degree of substitution are obtained on completion of the viscose spinning process. Fibers such as these are commercially available from FMC Corporation under the trademark BAR (Bondable Avisco Rayon) fibers.

Other reagents suitable for uniformly modifying the viscose by addition to the viscose solution during xanthogenation are sodium vinyl sulfonate, sodium chloromethane sulfonate, and sodium chloromethane phosphonate. Uniformly chemically modified viscose fibers containing sulfoethyl groups, sulfomethyl groups and phosphonomethyl groups are obtained in this way.

However, a fibrous cellulose chemically modified throughout by carboxyl groups and, more especially, by carboxymethyl groups is particularly preferred for producing the sanitary hygiene aids according to this invention. A fibrous material obtained from a carboxymethyl-modified cellulose regenerated by the viscose spinning process is especially suitable.

The cellulose derivatives suitable for producing the fibrous material to be used in accordance with this invention should have such a high degree of substitution, based on the anionic salt-forming groups, that they are capable of binding from 0.1 to 3.0% by weight of copper, based on the weight of the fibrous material. The most suitable carboxymethyl-modified viscose fibers for the fibrous material according to the invention have a degree of substitution of from 0.01 to 0.3, i.e.; they contain on average from about 0.01 to 0.3 carboxymethyl groups per anhydroglucose unit. The content of bound copper should make up from 0.2 to 2.0% by weight and preferably from 0.6 to 1.6% by weight of the fibrous material.

It has also proved to be of advantage for the fibrous material used in accordance with the invention to have a fiber pH-value, as measured in accordance with German Industrial Norm (DIN) 54,275, of from 4 to 5. The effect of a fiber pH of this order is that the fibrous materials according to the invention have a certain buffer effect on absorbed body liquids and thus establish a physiologically favorable, mildly acidic pH on the skin surface, so that inflammation and susceptibility to alkaliphilic microbial disorders are avoided.

The fibrous material to be used for the sanitary hygiene aids according to the invention should have—in another preferred embodiment—a high water retention capacity of at least 80%, as measured in accordance with DIN 53,814.

The fibrous material used in accordance with the invention may readily be produced from known fibers containing anionic salt-forming moieties by treating the fibers containing anionic salt-forming moieties with an aqueous cupric ($Cu^{+2}$) salt solution and washing the fibers with water until they are substantially free from salt, followed by drying.

The high water retention fibrous material preferably employed may readily be produced by using a carboxymethyl viscose fiber having a degree of substitution of from 0.01 to 0.3 and a correspondingly high water retention capacity. For example, the commercially available VISCOSORB lS fibers (a trademark of Lenzing AG) having a water retention capacity of approximately 200% and a degree of substitution of about 0.1, may be used either in the sodium salt form or after conversion into the free acid form.

In producing the fibers used in this invention, any cupric salt may be used, provided that it is water soluble, has an anion which can be displaced in an ionexchange reaction with the anionic salt-forming moieties of the modified cellulose fibers, and is physiologically compatible. The anionic salt-forming moieties of the modified cellulose fibers are preferably capped with hydrogen cations, although other cations may be employed, depending upon the cupric salt used and the presence of an acid. The use of a physiologically compatible cupric salt is only important because residual traces of the cupric salt may remain in the cellulose fiber after treatment. Useful cupric salts are the chloride, nitrate, sulfate, or acetate, or the carbonate, oxide, or hydroxide, depending upon the treatment method, with cupric sulfate being preferred. Of course, once the cupric cation is attached to the anionic moiety of the cellulose fiber, the manner of production is irrelevant to the finished fiber. A solution of from 1 to 20 g/l of cupric sulfate ($CuSO_4 . 5 H_2O$) in water is one example of a particularly suitable aqueous cupric salt solution. The treatment is generally carried out in the absence of heat for a period of 1 to 60 minutes, 20 to 40 minutes being preferred. Thereafter, the copper salt solution is removed from the fiber, for example by pressing, the fiber is washed with water until the washing water is substantially free from sulfate ions, the water is removed from the fiber by further pressing, and the fiber is dried in a stream of air. The fibrous material having a fiber pH of from 4 to 5 used in accordance with the invention may readily be obtained by this process providing cupric salt solution adjusted with an acid to a pH-value of from 4 to 5 is used.

The fibrous material used in accordance with the invention has a more or less pronounced blue coloration, depending on the quantity of copper attached. This blue color, which cannot be washed out under practical conditions, does not affect the use according to the invention in sanitary, hygiene aids and is entirely consistent with psychological perceptions of hygiene.

The described fibers may readily be processed, by standard methods, into the sole or partial ingredient of: a catamenial device such as a tampon, sanitary napkin, panty shield or panty liner; a device for application to non-catamenial blood or lymph such as a bandage, swab, or tampon for dental and medical surgery; a device for application to urine such as a baby diaper or similar device for incontinent adults; or a device for application to perspiration such as a shoe liner, dress shield, sweat pad, or sweat band.

The bound copper-impregnated fibrous materials are preferably processed on their own, but also may be admixed with other fibers, to form the hygiene aids according to the invention. The hygiene aids according to the invention have the major advantage that bacteria, particularly those encountered in intimate body regions, for example *Escherichia coli; Staphylococcus aureus* and *Candida albicans,* do not proliferate in the hygiene aids, even under optimal incubation conditions. Even after incubation for 3 days, nutrient cultures charged with the fibrous materials used in accordance with the invention did not emit the unpleasant characteristic odor of corresponding cultures charged with normal wadding.

Since the copper is firmly attached to the anionic and electronegative groups of the fibers, there is no danger of the copper salt being dissolved by bodily secretions to reach the skin or mucosa in relatively high concentrations and producing toxic side effects.

The invention is illustrated by the following Examples:

EXAMPLES

A. Production of the deodorizing and microbistatic fibrous material used in this invention (Examples 1-2)

EXAMPLE 1

1 kg of carboxymethylated viscose fibers of the Viscosorb lS type having a degree of substitution of 0.09 to 0.10 was treated for 30 minutes at room temperature (20° C.) with 20 l of a solution of 20 g of $CuSO_4.5\ H_2O$ in 1000 ml of water of which the pH-value had been adjusted to 5 with dilute sulfuric acid. The fibers were then squeezed to a moisture content of 200% and washed with water until the washing water was free from sulfate. They were then squeezed again to a moisture content of 200% and dried for 4 hours at 105° C. in a recirculating-air drying chamber. The fibrous material obtained had a fiber pH of 5.6 (as measured in accordance with DIN 54,275), a copper content of 1.45% by weight and a water retention capacity of 87% (as measured in accordance with DIN 53,814).

EXAMPLE 2

1 kg of carboxymethylated viscose fibers of the Viscosorb lS type having a degree of substitution of 0.10 was converted into the acid form by treatment with a 0.2% aqueous hydrochloric acid solution (for 30 minutes at room temperature—20° C.) and then washing out the excess hydrochloric acid. The fibers squeezed to a moisture content of around 200% were then treated for 30 minutes at room temperature (20° C.) with a solution of 5 g of $CuSO_4.5\ H_2O$ in 1000 ml of water of which the pH-value had been adjusted to 4.5 with dilute sulfuric acid. Processing was carried out in the same way as in Example 1. The fibrous material obtained had a fiber pH of 4.2 (as measured in accordance with DIN 54,275), a copper content of 0.64% by weight and a water retention capacity of 109.5% (as measured in accordance with DIN 53,814).

EXAMPLE 3

Production of tampons from the deodorizing and microbistatic fibrous material according to Example 1

As is normal in tampon manufacture, the fibrous material was opened out on a card and processed into web-form wadding having a weight per unit area of approximately 630 g/m². The wadding was stabilized by needle punching.

The recovery cord was stitched longitudinally onto 40×90 mm strips of the wadding. After conditioning in a conditioning chamber (20° C./65% relative air humidity), the strips were axially and radially compressed by the Tampax process. The fibrous material could be processed without difficulty and produced very good tampons.

EXAMPLE 4

Demonstration of the prevention of bacterial growth and of the deodorizing effect:

Germs tested:
*Staph. aureus*
*E. coli*
*Ps. aeruginosa*
*Proteus mirabilis*
*Candida albicans*

Test procedure:

Quantities of 10 ml of CASO culture broth were added to quantities of 1 g of normal viscose (3.6 dtex, 30 mm) made by Hoechst and of copper-impregnated fibrous material according to Examples 1 and 2 in test tubes. The test tubes thus prepared were inoculated with quantities of 0.1 ml of germ suspension (see above) -24 h broth culture diluted in a ratio of 1:100 - 25 and incubated at 37° C.

Result:

In the case of the normal viscose, growth occurred with each strain (see above), whereas in none of the copper-impregnated fibrous materials could growth be detected, even after 72 h. At the same time, odor emission was only observed in the case of the cultures charged with normal viscose, corresponding to the normal broth cultures of the corresponding germs. The cultures charged with the special waddings did not emit any odor.

EXAMPLE 5

Testing of the deodorizing effect with reference to the example of menstrual blood Menstrual blood was collected from various test subjects using a special apparatus.

Quantities of 0.5 ml of fresh menstrual blood were added to quantities of 250 mg of the fibrous materials of Examples 1 and 2 and to normal viscose and incubated in a moist chamber at 37° C. Odor emission was assessed immediately after addition of the menstrual blood and also after 2, 4, 6 and 24 hours. In every case, odor emission was evaluated by 6 examiners. At all times, the samples of the copper-impregnated fibrous materials were judged to be considerably better. In contrast to the normal wadding, the copper-impregnated waddings did not emit the typical nauseating odor; only a faint herbal odor occurred after relatively long periods of incubation.

EXAMPLE 6

Testing of odor emission with reference to the example of ox blood

Quantities of 3 g of normal viscose and copper-impregnated fibrous material according to Examples 1 and 2 were incubated at 37° C. with 10 ml of ox blood. The results correspond to those described in Example 5. The only difference was that some of the incubation times were longer, depending on the initial condition of the blood.

EXAMPLE 7

Testing as an absorbent material in a panty shield

A 250 g/m$^2$ web of wadding was prepared from the fibrous material of example 2 in the usual way by opening out on a card, the carded web being stabilized by needle punching. 50×150 mm strips (standard panty shield format) were punched out, wrapped in a nonwoven covering (20 g/m$^2$, polypropylene) and the back covered with a film of polyethylene. Shields of normal viscose were produced in the same way. The maximum absorption capacity was tested in a sanitary napkin tester.

To this end, the shield was placed around a semicircular plastic molding, which had a central hole at its lower end, and fixed by a strip of film. Running movements were simulated by two plastic jaws which moved back and forth in the test at a rate of 106 strides per minute. The pressure exerted on the shield by the moving jaws amounted to 160 g on each side. The liquid was then applied dropwise through the opening in the plastic molding until the first drop had laterally penetrated (2 ml/min., test liquid water). No differences could be detected with the limits of error between the samples of normal viscose and copper-impregnated fibrous material. Values of 18–22 ml/shield were measured for both types (10 shields of each material were tested).

We claim:

1. A method for absorbing bodily secretions while hindering the generation of odors and growth of microbes comprising applying to said secretions at or near their source, an effective amount of a fibrous material consisting at least partially of viscose cellulose fibers substituted uniformly by anionic moieties of at least one of the general formulae: $-PO_3H^{(-)}$; $-(CH_2)_n-PO_3H^{(-)}$; $-(CH_2)_n-SO_3^{(-)}$; or $-(CH_2)_n-COO^{(-)}$; wherein n is from 1 to 3; which anionic moieties are each attached through an oxygen atom to a viscose cellulose anhydroglucose unit; wherein sufficient of said anionic moieties are present, and sufficient of said present anionic moieties are bonded to cupric cations, that said viscose cellulose fibers bind from about 0.1 to about 3% by weight of copper, based on the weight of said fibers.

2. The method of claim 1 wherein in said viscose cellulose fibers the degree of substitution of said fiber by said anionic moiety is about 0.01 to 0.3.

3. The method of claim 1 wherein in said viscose cellulose fibers the bound copper content is about 0.2 to about 2.0% by weight, based on the weight of said fibers.

4. The method of claim 2 wherein in said viscose cellulose fibers the bound copper content is about 0.2 to about 2.0% by weight, based on the weight of said fibers.

5. The method of claim 1 wherein in said viscose cellulose fibers the bound copper content is about 0.6 to about 1.6% by weight, based on the weight of said fibers.

6. The method of claim 2 wherein in said viscose cellulose fibers the bound copper content is about 0.6 to about 1.6% by weight, based on the weight of said fibers.

7. The method of claim 1 wherein said cellulose fibers consist essentially of viscose fibers uniformly substituted by carboxymethyl anions.

8. The method of claim 6 wherein said cellulose fibers consist essentially of viscose fibers uniformly substituted by carboxymethyl anions.

9. The method of claim 1 wherein said fibrous material has a fiber pH of about 4 to 5.

10. The method of claim 4 wherein said fibrous material has a fiber pH of about 4 to 5.

11. The method of claim 8 wherein said fibrous material has a fiber pH of about 4 to 5.

12. The method of claim 1 wherein said fibrous material has a water retention capacity of more than 80%.

13. The method of claim 10 wherein said fibrous material has a water retention capacity of more than 80%.

14. The method of claim 11 wherein said fibrous material has a water retention capacity of more than 80%.

15. The method of claim 1 wherein said cellulose fibers consist essentially of viscose fibers uniformly modified by carboxymethyl anions, having a water retention capacity of approximately 200% and a degree of substitution of about 0.10.

16. The method of claim 5 wherein said cellulose fibers consist essentially of viscose fibers uniformly modified by carboxymethyl anions, having a water retention capacity of approximately 200% and a degree of substitution of about 0.10.

17. The method of claim 1 wherein said bodily secretions are catamenia and said fibrous mass is in the form of a catamenial device.

18. The method of claim 17 wherein said catamenial device is a tampon, sanitary napkin, panty shield or panty liner.

19. The method of claim 4 wherein said bodily secretions are catamenia and said fibrous mass is in the form of a catamenial device.

20. The method of claim 19 wherein said catamenial device is a tampon, sanitary napkin, panty shield or panty liner.

21. The method of claim 15 wherein said bodily secretions are catamenia and said fibrous mass is in the form of a catamenial device.

22. The method of claim 21 wherein said catamenial device is a tampon, sanitary napkin, panty shield or panty liner.

23. The method of claim 1 wherein said bodily secretions are non-catamenial blood or lymph and said fibrous mass is in the form of a bandage, swab, or tampon for dental and medical surgery.

24. The method of claim 15 wherein said bodily secretions are non-catamenial blood or lymph and said fibrous mass is in the form of a bandage, swab, or tampon for dental and medical surgery.

25. The method of claim 16 wherein said bodily secretions are non-catamenial blood or lymph and said fibrous mass is in the form of a bandage, swab, or tampon for dental and medical surgery.

26. The method of claim 1 wherein said bodily secretions are urine and said fibrous mass is in the form of a baby diaper or similar device for incontinent adults.

27. The method of claim 15 wherein said bodily secretions are urine and said fibrous mass is in the form of a baby diaper or similar device for incontinent adults.

28. The method of claim 16 wherein said bodily secretions are urine and said fibrous mass is in the form of a baby diaper or similar device for incontinent adults.

29. The method of claim 1 wherein said bodily secretions are perspiration and said fibrous mass is in the form of a shoe liner, dress shield, or sweat pad or band.

30. The method of claim 15 wherein said bodily secretions are perspiration and said fibrous mass is in the form of a shoe liner, dress shield, or sweat pad or band.

31. The method of claim 16 wherein said bodily secretions are perspiration and said fibrous mass is in the form of a shoe liner, dress shield, or sweat pad or band.

* * * * *